United States Patent [19]

Ishizaka

[11] 4,235,099

[45] Nov. 25, 1980

[54] ULTRASONIC APPARATUS AND METHOD FOR MEASURING THE DENSITY OF LIQUID

[75] Inventor: Hideo Ishizaka, Fujinomiya, Japan

[73] Assignee: Terumo Corporation, Tokyo, Japan

[21] Appl. No.: 33,527

[22] Filed: Apr. 26, 1979

[30] Foreign Application Priority Data

Dec. 27, 1978 [JP] Japan .............................. 53/163291

[51] Int. Cl.$^3$ ............................................. G01N 9/00
[52] U.S. Cl. ................................................ 73/32 A
[58] Field of Search ..................................... 73/32 A

[56] References Cited

U.S. PATENT DOCUMENTS

| 3,486,381 | 12/1969 | Farese ............................ 73/32 A |
| 3,555,880 | 1/1971 | Menius, Jr. et al. ............. 73/32 A |
| 3,789,655 | 2/1974 | Passeri ............................ 73/24 |
| 4,132,110 | 1/1979 | Muramoto ....................... 73/32 A |

FOREIGN PATENT DOCUMENTS

| 1110866 | 10/1955 | France ............................. 73/24 |
| 456996 | 3/1975 | U.S.S.R. ........................ 73/32 A |

*Primary Examiner*—S. Clement Swisher
*Attorney, Agent, or Firm*—Frishauf, Holtz, Goodman & Woodward

[57] ABSTRACT

Ultrasonic waves are applied to a test liquid of an unknown density, and the acoustic parameters of the liquid are measured. The difference is then detected between the acoustic parameters of the test liquid and those of a standard liquid of the same temperature. The difference thus detected is added to the known density of the standard liquid, thereby obtaining the density of the test liquid.

9 Claims, 6 Drawing Figures

ULTRASONIC APPARATUS AND METHOD FOR MEASURING THE DENSITY OF LIQUID

BACKGROUND OF THE INVENTION

This invention relates to an apparatus and method for measuring the density of a liquid, using ultrasonic waves.

A method is known which uses ultrasonic waves to measure the density of a liquid. In the known method, ultrasonic waves are emitted to pass through a liquid of an unknown density, and the so-called "sing-around method" or the other methods are used to detect the period of time in which the waves pass through the liquid. Based on the period of time thus detected, the density of the liquid is calculated. With this method, however, the density of a liquid is erroneously measured due to the variation of external factors such as temperature.

It is an object of this invention to provide an apparatus and method which can accurately measure the density of a liquid, using ultrasonic waves, not affected by external factors.

SUMMARY OF THE INVENTION

According to this invention, ultrasonic waves are emitted to pass through a standard liquid of a known density and a liquid of an unknown density. The periods of time in which the waves travel through these liquids are detected, or the speeds at which they travel through the liquids are detected. The difference between the liquids in respect to the period of time or the traveling speed is then obtained. Based on the difference thus obtained, the density difference between the liquids is obtained. The density difference is added to the density of the standard liquid at a specific temperature, whereby the density of the other liquid at the specific temperature is measured.

DETAILED DESCRIPTION

Figure 1:
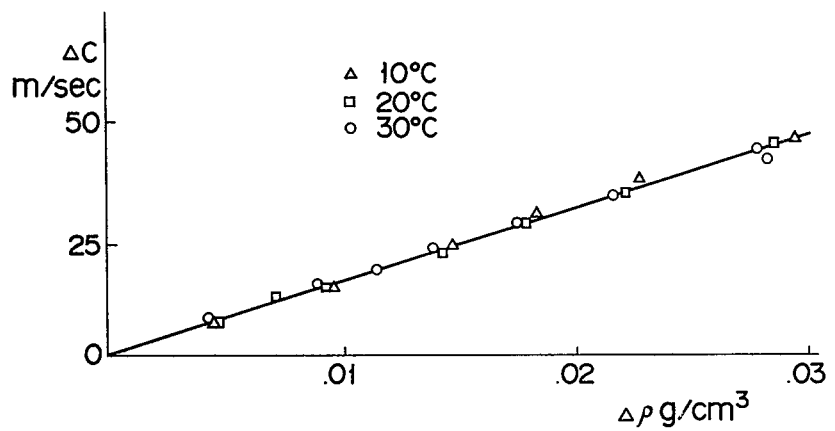
FIG. 1 shows the relationship between the density difference between water and a solution of salt and the difference between water and solution of salt in respect to the speed of sound traveling through them.

The density of a substance and the speed of sound traveling through the substance have such a relationship expressed as $Z = \rho C$, where $\rho$ denotes the density, $C$ the speed of sound and $Z$ the acoustic impedance of the substance.

The permeability of acoustic waves traveling from a substance haveing an acoustic impedance $Z$ to a substance A having an acoustic impedance $Z_A$ is represented as $2Z_a/Z+Z_A$. Similarly, the permeability of acoustic waves traveling from the substance having acoustic impedance $Z$ to another substance B having an acoustic impedance $Z_B$ is expressed as $2Z_B/Z+Z_B$. If the substances A and B are of the same temperature and have extremely similar acoustic characteristics, the difference $\Delta P$ between said permeabilities of acoustic waves is represented as follows:

$$\Delta P = \frac{2Z_A}{Z+Z_A} - \frac{2Z_B}{Z+Z_B} = \frac{2Z(Z_A - Z_B)}{(Z+Z_A)(Z+Z_B)} \quad (1)$$

The following equations are established with regard to a solid solution or solution B consisting of a pure solvent A and a little amount of one solute:

$$Z_B = Z_A + \Delta Z,$$

$$C_B = C_A + \Delta C,$$

$$\rho_B = \rho_A + \Delta \rho.$$

If $Z_A \gg \Delta Z$, $C_A \gg \Delta C$ and $\rho_A \gg \Delta \rho$, the difference $\Delta P$ between said permeabilities of acoustic waves is expressed as follows:

$$\Delta P \approx \frac{-2Z\Delta Z}{(Z+Z_A)^2} \quad (2)$$

$$\Delta Z = C_A \Delta \rho + \rho_A \Delta C + \Delta \rho \Delta C \approx C_A \Delta \rho + \rho_A \Delta C$$

$$\therefore \Delta P = -\frac{2Z}{(Z+Z_A)^2}(C_A \Delta \rho + \rho_A \Delta C)$$

If the solution B is at a constant temperature and under a constant pressure, the amount of the solute, though very little, determines the difference $\Delta C$ of speed of sound and the density difference $\Delta P$. More specifically, the amount of the solute is proportional to $\Delta C$ and $\Delta \rho$. Here let K denote proportional constant. Then, $\Delta C$ is represented as follows:

$$\Delta C = K\Delta \rho \propto \text{amount of solute (concentration of solution)} \ldots \quad (3).$$

Equation (2) can therefore be transformed into the following eqaution (4):

$$\Delta P = \frac{2Z}{(Z+Z_A)^2}(C_A + K\rho_A)\Delta \rho \quad (4)$$

In equation (4), the coefficient to the density difference $\Delta \rho$ denotes not change so long as the temperature and pressure remain unchanged and the solute or solvent is not replaced with another one. Thus, if the difference $\Delta P$ between two similar substances with respect to speed of sound traveling through them is measured, the density difference between the substances can be obtained. Proportional constant K depends on which substance is used as solute. Equation (4) applies when only one solute is dissolved in the solvent to form a solution. Nevertheless, equation (4) can apply even when two or more solutes are dissolved in the solvent if proportional constant K remains substantially unchanged. For example, proportional constant K of a solution consisting water and one solute such as saccharose, lactose, KCl and HCl is quite similar to proportional constant K of a solution consisting water and two or more of such solutes, if the density difference $\Delta\rho$ between water and the solution falls within the range of $0 \lesssim \Delta\rho \lesssim 0.04$.

Thus far described in the relationship between the density of a substance and the speed of sound traveling through the substance. Based on the speed of acoustic waves reflected from a substance, it is also possible to obtain the density difference between two substances in a similar method. If acoustic waves emitted to a thick plate comprised of two or more layers of different substances, they partly pass through each layer and are partly reflected from each layer. The formula by which to obtain the difference $\Delta P$ between the permeability of waves to one layer and the permeability of waves to another layer is considerably complicated. But an equation similar to equation (4) stands to prove that $\Delta P$ between one layer and another is proportional to the density difference $\Delta\rho$ the substances of these layers. The speed C of acoustic waves passing through a substance is represented as follows:

$$C = \sqrt{\frac{E}{\rho}}, \; E: \text{bulk modulus}, \rho: \text{density}.$$

The following equations are established with regard to a solution B consisting of a pure solvent A and a little amount of one solute:

$$E_B = E_A + \Delta E,$$

$$\rho_B = \rho_A + \Delta\rho.$$

If $E_A \gg \Delta E$ and $\rho_A \gg \Delta\rho$, the difference $\Delta C$ between the speed of sound traveling through the solvent A and the speed of sound traveling through the solution B is expressed as follows:

$$\Delta C = C_A - C_B \tag{5}$$
$$= \sqrt{\frac{E_A}{\rho_A}} - \sqrt{\frac{E_B}{\rho_B}}$$
$$= \sqrt{\frac{E_A}{\rho_A}} - \sqrt{\frac{E_A + \Delta E}{\rho_A + \Delta\rho}}$$
$$= \sqrt{\frac{E_A}{\rho_A}} \left(1 - \sqrt{1 + \frac{\Delta E}{E_A} - \frac{\Delta\rho}{\rho_A}}\right)$$
$$= \tfrac{1}{2}\sqrt{\frac{E_A}{\rho_A}} \left(\frac{\Delta\rho}{\rho_A} - \frac{\Delta E}{E_A}\right)$$

The concentration of the solution B is perfectly proportional to $\Delta\rho$ and $\Delta E$. Thus:

$$\Delta E = K'\Delta\rho \ldots \tag{6}$$

Equations (5) and (6) are combined to form the following equation:

$$\Delta C = \tfrac{1}{2}\sqrt{\frac{E_A}{\rho_A}} \left(\frac{1}{\rho_A} - \frac{K'}{E_A}\right)\Delta\rho \tag{7}$$

Equation (7) corresponds to equation (3) which shows that the difference $\Delta C$ is proportional to the density difference $\Delta\rho$. Proportional constant K' in equation (7) is almost not affected by the temperature.

FIG. 1 shows that $\Delta C$ between water and solution of salt is proportional to $\Delta\rho$ between water and solution of salt. As FIG. 1 clearly shows, proportional constant K is almost not affected by temperature over the range from 10° C. to 30° C.

Let $t_A$ denote the period of time necessary for acoustic waves to pass through a substance A for a distance l, and $t_B$ the period of time necessary to acoustic waves to pass through a substance B for the same distance l. Then, the difference $\Delta t$ between $t_A$ and $t_B$ is obtained as follows:

$$\Delta t = t_A - t_B = -\frac{l}{2}\sqrt{\frac{\rho_A}{E_A}}\left(\frac{1}{\rho_A} - \frac{K'}{E_A}\right)\Delta\rho \tag{8}$$

Suppose the substance A is a standard liquid of a known density and that the substance B is a liquid of an unknown density. Then, the density difference between the liquids is proportional to the difference in sound pressure between the acoustic waves traveling through the standard liquid and the acoustic waves traveling through the liquid of unknown density, the speed difference between the sound traveling through the standard liquid and the sound traveling through the liquid of unknown density, or the difference between the period of time necessary for the acoustic waves to pass through the standard liquid for a specific distance and the period of time necessary to the acoustic waves to pass through the liquid of unknown density for the specific distance. The density difference can therefore be obtained only if there is prepared a table showing the relationship between the density difference and the difference in such acoustic parameters as mentioned above.

The standard liquid is not limited to a pure solvent. Any solution may be used as the standard. For example, solution of salt having a high concentration may be used. In many cases, water is used as the standard liquid. Since the acoustic parameters of water have a specific relationship with the resistance value of a thermistor, this invention uses a thermistor instead of a standard liquid so as to measure the density of a liquid.

Now referring to FIGS. 2 to 5, a few embodiments of this invention will be described.

Figure 2:
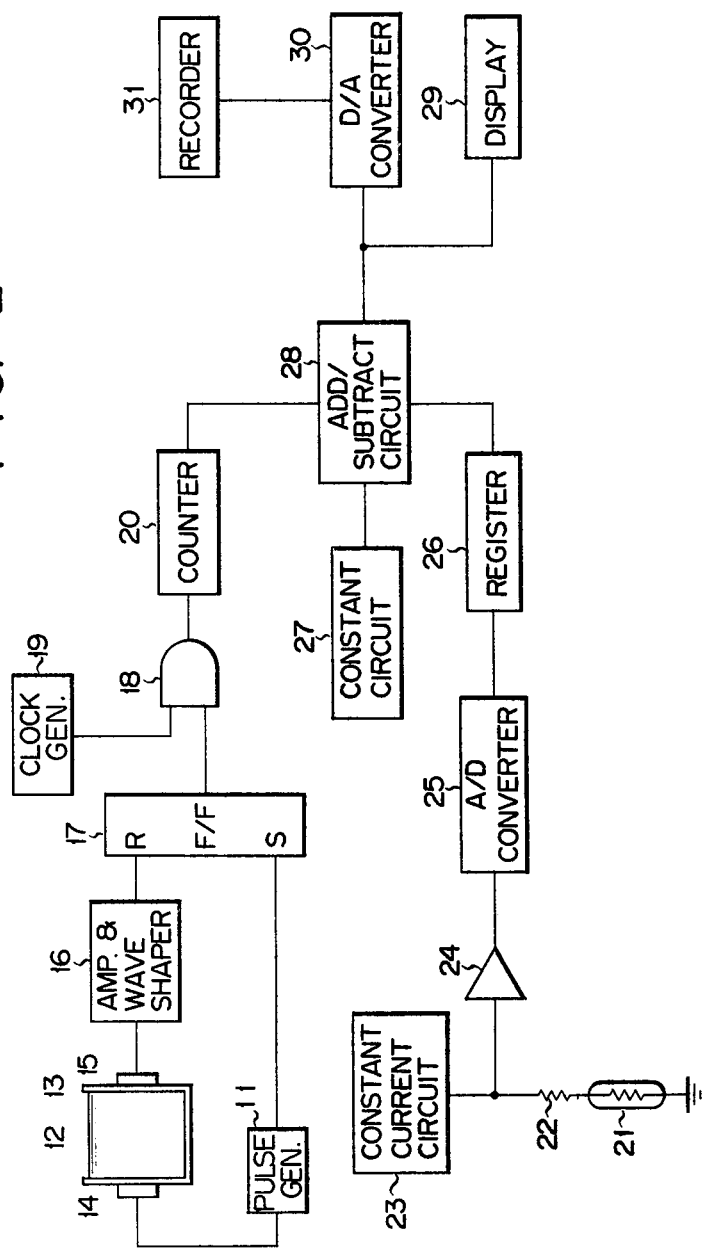
FIG. 2 is a block circuit diagram of an ultrasonic apparatus according to this invention for measuring the density of liquid.

In the embodiment of FIG. 2, the output of a pulse generator 11 is connected to an ultrasonic transmitter 14 which is attached to a tank 13 containing a liquid of an unknown density. On one side of the tank 13, which faces the side of which the transmitter 14 is attached, an ultrasonic receiver 15 is provided. The output of the receiver 15 is coupled to an amplifier-waveform shaping circuit 16. The output of the circuit 16 is coupled to the reset terminal of an flip-flop 17. The set terminal of the flip-flop 17 is connected to the output of the pulse generator 11. The output of the flip-flop 17 is connected to one input terminal of an AND gate 18. The other input terminal of the AND gate 18 is connected to the output terminal of a clock pulse generator 19. The output terminal of the AND gate 18 is connected to a counter 20.

A thermistor 21 is attached to the tank 13. The thermistor 21 has one end connected to the ground and the other end connected via a resistor 22 to a constant current source 23 and an amplifier 24. The output of the amplifier 24 is coupled via an A/D converter 25 to a register 26. The output of the register 26, the output of the counter 20 and the output of a constant input device 27 are coupled to an adder-subtracter circuit 28. The output of the circuit 28 is coupled to a display device 29 and to a recorder 31 via a D/A converter 30.

Figure 3:
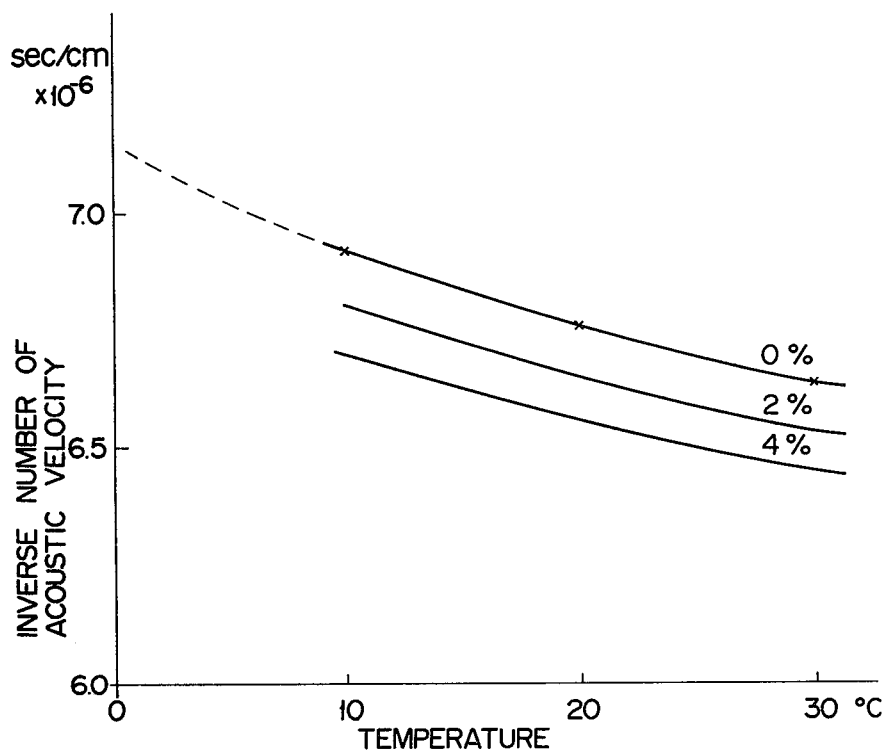
FIG. 3 illustrates the relationship between the temperature of water and solution of salt and the speed of sound traveling through them, which is expressed in reciprocal numbers.

The thermistor 21 and the resistor 22 constitute a series circuit, which is used as a standard. FIG. 3 shows the speeds of sound in water, 2% salt solution and 4% salt solution—all expressed in reciprocal numbers. The curves are obtained by a series circuit of a thermistor and a fixed resistor. In practice, thermistor TM-550 manufactured by Hitachi Ltd., Japan and a 45.14 K$\Omega$ resistor may be used, and the resistance of the series circuit constituted by these thermistor and resistor is multiplied by $1.421 \times 10^{-10}$ sec/cm·$\Omega$. That is, the series circuit of a thermistor and a resistor shows acoustical characteristics equivalent to those of water which is generally used as a standard liquid.

The pulse generator 11 generates 1 KHz pulse signals. A 1 KHz pulse signal sets the flip-flop 17 and energizes the transmitter 14. The transmitter 14 generates ultrasonic waves, which are transmitted via the liquid 12 to the receiver 15. The receiver 15 converts the ultrasonic waves into an electric signal. The electric signal thus obtained is supplied to the amplifier-waveform shaping circuit 16. The circuit 16 amplifies the electric signal and rectifies the waveform of the signal. The output signal of the circuit 16 is supplied as a trigger pulse to the reset terminal of the flip-flop 17, thus resetting the flip-flop 17. Thus, the flip-flop 17 is set when the transmitter 14 starts emitting ultrasonic waves and is reset when the receiver 15 receives the ultrasonic waves. That is, the flip-flop 17 is kept in set state for the period of time during which the ultrasonic waves travel through the liquid 12 from the transmitter 14 to the receiver 15.

The output pulse of the flip-flop 17 is supplied to the AND gate 18. So long as the AND gate 18 is opened by the output pulse of the flip-flop 17, the clock pulses are supplied from the clock pulse generator 19 to the counter 20. The counter 20 therefore counts the period of time during which the ultrasonic waves travel through the liquid 12.

The voltage on the series circuit for the thermistor 21 and the fixed resistor 22 is amplified by the amplifier 24 and converted by the A/D converter 25 into a digital signal. This digital signal is written into the register 26. The A/D converter 25 is so designed as to produce an output every time the pulse generator 11 generates a pulse signal. The data stored in the register 26 represents acoustic parameters equivalent to those of a standard liquid, for example, water. The data is transferred to the adder-substractor circuit 28. The circuit 28 obtains the difference between the acoustic parameters of the standard liquid and the count of the counter 20., i.e. acoustic parameters of the liquid 12. The output of the constant input device 27, which is a digital value showing the density of the standard liquid at a give temperature, is added to the difference between the acoustic parameters of the standard liquid and those of the liquid 12. As a result, the adder-substractor circuit 28 produces a digital data which represents the density of the liquid 12 at the given temperature. This data is displayed by the display device 29, and it is converted by the D/A converter 30 into an analog data. The analog data is recorded by the recorder 31.

As mentioned above, based on the resistance value of a thermistor provided in contact with the liquid of an unknown density, there is detected the period of time during which ultrasonic waves travel through a standard liquid of the same temperature as the liquid of unknown density. Then, the difference between the period of time thus detected and the period of time during which ultrasonic waves travel through the liquid of unknown density is obtained. To this difference the density of the standard liquid at the same temperature is added, thereby obtaining the density of the test liquid.

In the above-described embodiment, the data showing various periods of time are processed digitally. Instead the data may be processed analogically. If this is the case, the clock pulse generator 19 is replaced by a constant voltage circuit, the counter 20 is replaced by a combination of an integral circuit and a sample-hold circuit, and the output of the amplifier 24 is supplied directly to the adder-substracter circuit 28.

Figure 4:
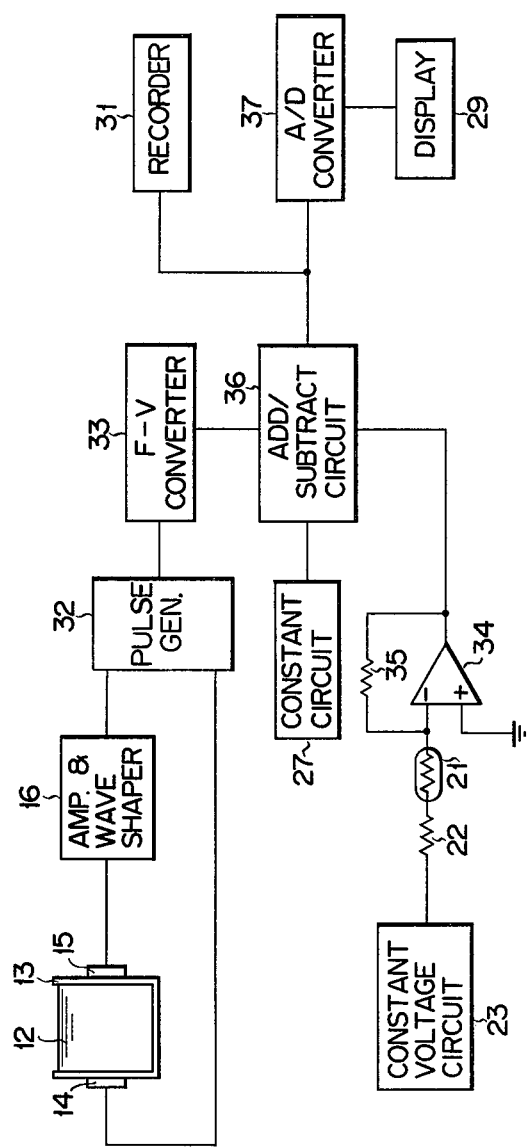
FIG. 4 is a block circuit diagram of another ultrasonic apparatus according to this invention for measuring the density of liquid.

FIG. 4 shows another embodiment of this invention. In this embodiment, a pulse generator 32 has its trigger input terminal connected to an ultrasonic receiver 15 via an amplifier-waveform shaping circuit 16 and its output terminal connected to an ultrasonic transmitter 14. The pulse generator 32 generates 1 Hz pulses if a tank 13 is emptly of a liquid 12 of an unknown density. If the tank 13 is full of the liquid 12, the receiver 15 produces pulses in response to the ultrasonic waves coming from the transmitter 14 through the liquid 12. Each output pulse of the receiver 15 is amplified, and its waveform is shaped by the amplifier-waveform shaping circuit 16. The output of the circuit 16 is supplied as a trigger pulse to the trigger input terminal of the pulse generator 32. When triggered, the generator 32 produces an output pulse which is therefore synchronous with the trigger pulse. The output pulse of the pulse generator 32 energizes the transmitter 14, thereby generating ultrasonic waves. The ultrasonic waves thus generated are transmitted to the receiver 15 through the liquid 12. Energized by the ultrasonic waves, the receiver 15 produces pulses. The amplifier-waveform shaping circuit 16 therefore amplifies these pulses and shapes their waveform. The output pulses of the circuit 16 are supplied back to the pulse generator 32. In this way the pulse generator 32 repeatedly generates pulses and receives pulses. The output pulses of the generator 32 are supplied to an F-V converter 33 and converted into voltage signals which correspond to the output frequency of the pulse generator 32.

The apparatus of FIG. 4 further comprises a thermistor 21 attached to the tank 13 and a resistor 22. The thermistor 21 and the resistor 22 constitute a series circuit which functions as a standard. The output of the series circuit is supplied to the inverting input of an operational amplifier 34. The noninverting input of the amplifier 34 is connected to the ground. Between the inverting input and output of the amplifier 34 there is connected a feedback resistor 35. The output voltage of the operational amplifier 34 is supplied to an adder-subtracter circuit 36 and is subtracted from the output voltage of the F-V converter 33. The voltage difference corresponds to the density difference between a standard liquid and the liquid 12. The voltage difference is added to the output of a constant input device 27, which represents the density of the standard liquid. Thus, the adder-subtracter circuit 36 produces an analog signal which corresponds to the density of the liquid 12. The analog signal is recorded by a recorder 31. Further, the analog signal is converted by an A/D converter 37 into a digital signal which is displayed by a display device 29.

Figure 5:
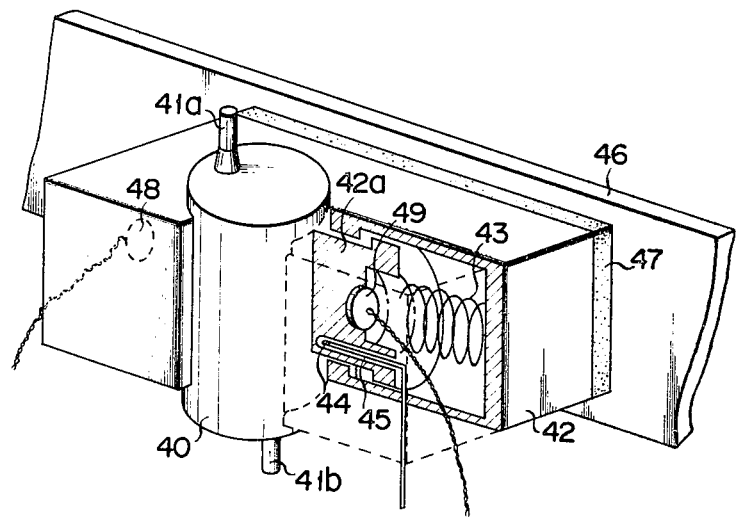
FIG. 5 is a perspective view of a liquid density measuring section of the ultrasonic apparatus shown in FIG. 2 or 4.

FIG. 5 illustrates a urine density measuring section of a urine gravimeter to which this invention is applied. The measuring section comprises a disposable urine container 40. Tubes 41a and 41b are connected to the top and bottom of the container 40, respectively. Urine is introduced into the container 40 through the tube 41a and is discharged through the tube 41b. The specific gravity of urine can therefore be measured continuously. The container 40 is held by a holder 42. The holder 42 includes a clamp member 42a which is biased onto the container 40 by means of a spring 43. The clamp member 42a has a hole 44, in which a thermistor 44 is disposed to detect the temperature of the urine in the container 40. An adhesive film or magnet 47 is provided on one side of the holder 42 so that the holder 42 is easily attached to the bedside 46. An ultrasonic transmitter 48 and an ultrasonic receiver 49 are attached to the holder 42.

The ultrasonic apparatus according to this invention is applied to measure not only the specific gravity of urine but also the specific gravities or densities of other liquids such as liquid medicine, blood and dialytic solution.

Figure 6:
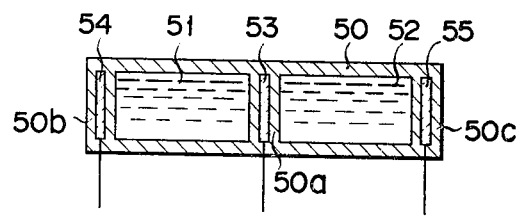
FIG. 6 is a cross sectional view of a liquid density measuring section of another embodiment.

In the above-described embodiments, a series circuit of a thermistor and a fixed resistor is used in place of a standard liquid. Instead, parallel circuit constituted by a thermistor and a fixed resistor may be employed. Further, such a two-chamber container 50 as shown in FIG. 6 may be used, without utilizing a thermistor or a fixed resistor. The container 50 includes a chamber 51 for containing a standard liquid and a chamber 52 for containing a liquid of an unknown density. In a partition 50a between the chambers 51 and 52 an ultrasonic transmitter 53 is provided, and in both sides 50b and 50c of the container 50 there are provided two ultrasonic receivers 54 and 55, respectively. From the output of the ultrasonic receiver 54 is detected the acoustic parameters of the standard liquid, while from the output of the ultrasonic receiver 55 is detected the acoustic parameters of the liquid of unknown density.

What is claimed is:
1. A method for measuring the density or specific gravity of a liquid, comprising steps of:
applying ultrasonic waves to a test liquid of an unkown density or an unknown specific gravity;
detecting ultrasonic waves after they pass through the test liquid, the detected ultrasonic waves being a function of the acoustic parameters of the test liquid;
detecting the difference between the acoustic parameters of the test liquid and those of a standard liquid of the same temperature as the test liquid; and
adding the detected difference to the known density or known specific gravity of the standard liquid of the same temperature as the test liquid to obtain the density or specific gravity of the test liquid.

2. An apparatus for measuring the density or specific gravity of a liquid, comprising:
a tank for containing a test liquid of an unknown density or an unknown specific gravity;
an ultrasonic transmitter attached to the tank for applying ultrasonic waves to the test liquid;
means including an ultrasonic receiver for receiving the ultrasonic waves coming from the ultrasonic transmitter through the test liquid for generating a first signal corresponding to the acoustic parameters of the test liquid;
means for producing a second signal which corresponds to the acoustic parameters of a standard liquid of a known density or a known specific gravity and of the same temperature as the test liquid;
means for generating a third signal corresponding to the known density or the known specific gravity of the standard liquid; and
an adder-subtractor circuit for receiving the first, second and third signals for generating a difference signal which corresponds to the difference between the acoustic parameters of the standard liquid and those of the test liquid, and for adding said difference signal to said third signal which corresponds to the known density or specific gravity of the standard liquid, to thereby obtain the density or specific gravity of the test liquid.

3. The apparatus according to claim 2, wherein said means for producing the second signal which corresponds to the acoustic parameters of the standard liquid comprises a fixed resistor, and a thermistor attached to the tank and having its resistance varied according to the temperature of the test liquid in the tank.

4. The apparatus according to claim 2, wherein said means for generating the third signal comprises means for detecting the period of time during which ultrasonic waves travel through the test liquid.

5. The apparatus according to claim 2, wherein said means for generating the third signal comprises means for detecting the speed at which ultrasonic waves travel through the test liquid.

6. An apparatus for measuring the density or specific gravity of liquid comprising:
a container having a first chamber for containing a standard liquid, a second chamber for containing a test liquid of an unknown density or unknown specific gravity, and a partition between the first and second chambers, the chambers having respective side walls;
an ultrasonic transmitter disposed in the partition between the first and second chambers;
two ultrasonic receivers disposed on side walls of the first and second chambers, respectively, to receive the ultrasonic signals transmitted from the ultrasonic transmitter after they pass through the liquid in the respective chambers;
means for detecting acoustic parameters of the standard liquid and the test liquid of unkown density or unknown specific gravity from the outputs of the ultrasonic receivers;
means for obtaining the difference between the detected acoustic parameters of the standard and test liquids; and
means for adding the detected difference to a known quantity representing the known density or specific gravity of the standard liquid to thereby obtain the density or specific gravity of the test liquid.

7. The apparatus according to claim 2, wherein said means for generating the third signal comprises a flip-flop circuit coupled to the ultrasonic transmitter and which is set when the ultrasonic transmitter starts emitting the ultrasonic waves, the flip-flop circuit being reset in response to the output signal of the ultrasonic receiver; and a counter coupled to the flip-flop circuit, the counter being triggered when the flip-flop circuit is set and reset when the flip-flop circuit is reset.

8. The apparatus according to claim 2, wherein said means for generating the third signal comprises a pulse generator coupled to the ultrasonic receiver for generating an output pulse in response to the output signal of the ultrasonic receiver and supplying the output pulse to the ultrasonic transmitter; and an F-V converter connected to the pulse generator for converting the output pulse of the pulse generator into a voltage signal which is supplied to the adder-subtractor circuit.

9. The apparatus according to claim 2 wherein said tank comprises a first chamber for containing a standard liquid; a second chamber for containing the test liquid; the chambers having respective side walls; and a partition between the first and second chambers, the ultrasonic transmitter being disposed in the partition between the first and second chambers, and respective ultrasonic receivers being disposed on side walls of the respective first and second chambers to receive ultrasonic signals transmitted from the ultrasonic transmitter after they pass through the liquid in the respective chambers, said ultrasonic receivers detecting the acoustic parameters of the test liquid and of the standard liquid.

* * * * *